United States Patent
Szypka

(10) Patent No.: US 7,833,377 B2
(45) Date of Patent: Nov. 16, 2010

(54) PROCESS FOR PREPARING AN ANIMAL INCONTINENCE DEVICE

(75) Inventor: Andrew J Szypka, Curtice, OH (US)

(73) Assignee: Principle Business Enterprises, Inc., Dunbridge, OH (US)

( * ) Notice: Subject to any disclaimer, the term of this patent is extended or adjusted under 35 U.S.C. 154(b) by 774 days.

(21) Appl. No.: 11/618,983

(22) Filed: Jan. 2, 2007

(65) Prior Publication Data

US 2008/0156433 A1    Jul. 3, 2008

(51) Int. Cl.
  *A01K 29/00*  (2006.01)
  *B31F 1/07*   (2006.01)
  *B32B 3/04*   (2006.01)

(52) U.S. Cl. .............. 156/209; 156/216; 156/276; 119/169; 119/171

(58) Field of Classification Search ............ None
See application file for complete search history.

(56) References Cited

U.S. PATENT DOCUMENTS

| | | | |
|---|---|---|---|
| 3,626,899 A | 12/1971 | Spellman | |
| 4,055,184 A | 10/1977 | Karami | |
| 4,260,443 A * | 4/1981 | Lindsay et al. | 156/220 |
| 4,551,191 A * | 11/1985 | Kock et al. | 156/276 |
| 4,774,907 A | 10/1988 | Yananton | |
| 4,800,677 A | 1/1989 | Mack | |
| 5,386,771 A * | 2/1995 | McCartney et al. | 101/148 |
| 5,630,376 A * | 5/1997 | Ochi et al. | 119/169 |
| 5,715,772 A | 2/1998 | Kamrath et al. | |
| 5,843,267 A * | 12/1998 | Cashaw et al. | 156/324 |
| 6,096,067 A | 8/2000 | Cramer et al. | |
| 6,227,145 B1 | 5/2001 | Miyamoto et al. | |
| 6,295,658 B1 | 10/2001 | Jenkins | |
| 6,336,935 B1 | 1/2002 | Davis et al. | |
| 6,544,386 B1 * | 4/2003 | Krzysik et al. | 162/123 |
| 6,582,413 B2 | 6/2003 | Krautkramer et al. | |
| 6,591,582 B2 * | 7/2003 | Weder | 53/397 |
| 6,635,799 B1 | 10/2003 | Osborn, III et al. | |
| 6,706,945 B1 | 3/2004 | Melius et al. | |
| 6,911,253 B2 | 6/2005 | Iwasa et al. | |
| 6,913,673 B2 * | 7/2005 | Baggot et al. | 162/117 |
| 2001/0044611 A1 | 11/2001 | Noda et al. | |
| 2002/0197346 A1 * | 12/2002 | Papadopoulos | 425/194 |
| 2003/0044562 A1 * | 3/2003 | Li et al. | 428/59 |
| 2003/0082966 A1 | 5/2003 | Menday et al. | |
| 2004/0033750 A1 | 2/2004 | Everett et al. | |
| 2004/0082246 A1 * | 4/2004 | Watanabe et al. | 442/327 |

\* cited by examiner

*Primary Examiner*—Richard Crispino
*Assistant Examiner*—Barbara J. Musser
(74) *Attorney, Agent, or Firm*—Fraser Clemens Martin & Miller LLC; J. Douglas Miller

(57) ABSTRACT

A process for preparing an animal incontinence device comprises: providing a base layer of tissue; applying a uniform layer of superabsorbent polymer particles to a major surface of the base layer of tissue; applying water to the base layer of tissue having the uniform layer of superabsorbent polymer particles thereon; applying a cover layer of tissue over the base layer of tissue having the uniform layer of superabsorbent polymer particles thereon, to form an absorbent layer assembly; passing the absorbent layer assembly between a heated nip roll and a laminating roll, to at least partially adhere together the cover layer of tissue, uniform layer of superabsorbent polymer particles, and base layer of tissue, to form an absorbent layer; inserting the absorbent layer intermediate a base layer of liquid-impervious polymer film and a top layer of porous, hydrophilic, woven or non-woven polymer fibers, to form an animal incontinence device assembly; and laminating together at least a portion of the animal incontinence device assembly.

21 Claims, No Drawings

PROCESS FOR PREPARING AN ANIMAL INCONTINENCE DEVICE

FIELD OF THE INVENTION

The present invention relates generally to a process for preparing an animal incontinence device. More particularly, the invention is directed to a process for preparing a multi-layered floor pad useful for absorbing animal urine.

BACKGROUND OF THE INVENTION

Devices for dealing with animal incontinence are known in the art. Such devices generally contain an absorbent layer of fibers or cellulose pulp. These devices are ineffective for absorbing and immobilizing animal urine, so that it is not squeezed out of the device and tracked by the animal over the floor.

It would be desirable to prepare an improved animal incontinence device that would absorb, contain, and immobilize the animal's urine.

SUMMARY OF THE INVENTION

Accordant with the present invention, a process for preparing an animal incontinence device that immobilizes the animal's urine has surprisingly been discovered. It comprises the steps of: providing a base layer of tissue; applying a uniform layer of superabsorbent polymer particles to a major surface of the base layer of tissue; applying water to the base layer of tissue having the uniform layer of superabsorbent polymer particles thereon; applying a cover layer of tissue over the base layer of tissue having the uniform layer of a superabsorbent polymer particles thereon, to form an absorbent layer assembly; passing the absorbent layer assembly between a heated nip roll and a laminating roll, to at least partially adhere together the cover layer of tissue, uniform layer of superabsorbent polymer particles, and base layer of tissue, to form an absorbent layer; inserting the absorbent layer intermediate a base layer of liquid-impervious polymer film and a top layer of porous, hydrophylic, woven or non-woven polymer fibers, to form an animal incontinence device assembly; and laminating together at least a portion of the animal incontinence device assembly.

The animal incontinence device according to the present invention is particularly useful for absorbing the urine of an incontinent animal, to keep the surrounding premises free from tracked urine.

DETAILED DESCRIPTION OF THE PREFERRED EMBODIMENTS

The present invention is directed to a process for preparing an animal incontinence device. It comprises the steps of: providing a base layer of tissue; applying a uniform layer of superabsorbent polymer particles to a major surface of the base layer of tissue; applying water to the base layer of tissue having the uniform layer of superabsorbent polymer particles thereon; applying a cover layer of tissue over the base layer of tissue having the uniform layer of superabsorbent polymer particles thereon, to form an absorbent layer assembly; passing the absorbent layer assembly between a heated nip roll and a laminating roll, to at least partially adhere together the cover layer of tissue, uniform layer of superabsorbent polymer particles, and base layer of tissue, to form an absorbent layer; inserting the absorbent layer intermediate a base layer of liquid-impervious polymer film and a top layer of porous, hydrophylic, woven or non-woven polymer fibers, to form an animal incontinence device assembly; and laminating together at least a portion of the animal incontinence device assembly.

The base layer of tissue that is provided according to the present invention may be conventional tissue paper made, for example, by removing water from a dilute suspension of cellulose fibers of wood, cotton, etc., resulting in the hydrogen bonding of the fibers together at their points of contact. Alternatively, the base layer of tissue may comprise multiple plies of tissue that have been treated to modify directional strength, surface texture, bulk, thickness, stretch properties, creep resistance, and the like. Methods for making and modifying tissue are well known in the art.

A uniform layer of superabsorbent polymer particles is applied to a major surface of the base layer of tissue. This may be accomplished by any conventional method such as, for example, by sprinkling the particles of superabsorbent polymer onto a web of the base layer of tissue that is continuously paid out from a supply roll at any conventionally operable line speed; preferably in the range from about 90 to about 120 meters per minute. By the term "uniform" as it is used herein is meant that the superabsorbent polymer particles are applied in a monolithic, evenly dispersed, continuous layer onto the base layer of tissue. The superabsorbent polymer particles may be applied to the base layer of tissue by any conventional method such as, for example, by sprinkling, spreading, fluidize conveying mechanical broadcasting, and the like.

The concentration of superabsorbent polymer particles may vary over wide operable limits, but preferably ranges from about 16 to about 20 grams per square meter. As will be readily apparent to one ordinarily skilled in the art, the concentration of superabsorbent polymer particles will depend upon the desired absorbing capacity for the animal incontinence device.

Superabsorbent polymers are cross-linked networks of flexible polymer chains. The most efficient water absorbers are polymer networks that carry dissociated ionic functional groups. Superabsorbent polymers work by diffusion on the molecular level. Water diffuses into the particles of superabsorbent polymer. The superabsorbent polymer swells to accommodate the additional molecules. Because the polymer molecules are cross-linked, they do not dissolve in the absorbed liquid. Commercially available superabsorbent polymer particles are well known in the art.

Water is applied to the base layer of tissue having the uniform layer of superabsorbent polymer particles thereon. This may conveniently be accomplished by spraying a mist of water onto the continuously moving web of tissue from above. The applied water at least partially wets the layer of tissue and the particles of superabsorbent polymer.

A cover layer of tissue is applied over the base layer of tissue having the superabsorbent polymer particles thereon, thus creating an absorbent layer assembly. This conveniently may be accomplished by paying out the cover layer of tissue from a supply roll, and overlaying the advancing web of base layer of tissue. The cover layer of tissue becomes at least partially wetted by the residual water applied in the previous step. The cover layer of tissue may be any of the materials disclosed for the base layer of tissue hereinabove. The cover layer of tissue used to make the absorbent layer assembly may be identical to the base layer of tissue in kind, number of plies, etc., or may be different.

Also contemplated by the present invention is an alternative process wherein any number of additional layers of superabsorbent polymer particles and cover layers of tissue may be applied over the basic absorbent layer assembly disclosed hereinabove. For example, following the application of the cover layer of tissue as set forth in the step immediately above, a second layer of superabsorbent polymer particles followed by a second cover layer of tissue may be applied over the initial cover layer of tissue. It is also contemplated that the applied water will be sufficient to at least partially wet all of the layers of superabsorbent polymer particles and tissue.

The absorbent layer assembly is passed between a heated nip roll and a laminating roll, to at least partially adhere together the components of the absorbent layer assembly, to thereby form an absorbent layer. The nip roll may be made of hard rubber or metal such as, for example, stainless steel or chrome-plated steel, and may be smooth or may contain an embossing pattern. A preferred nip roll imparts an embossed pattern to the exposed major surface of the base layer of tissue, thereby causing the ultimately produced absorbent layer to be more pliable and less stiff when processed with other materials in subsequent steps. The nip roll may be heated to a temperature from about 130 to about 190 degrees F. Preferably, the operating temperature of the nip roll ranges from about 160 to about 170 degrees F.

The laminating roll preferably employs a soft material at the nip, to apply pressure to the absorbent layer assembly without crushing the superabsorbent polymer particles. For example, the laminating roll may be a metal roll covered with a paper or cloth material, or may comprise a spongy rubber. The nip pressure, between the nip roll and the laminating roll, may vary from about 35 to about 75 psi. Preferably, the nip pressure ranges form about 50 to about 60 psi.

The absorbent layer is then inserted intermediate a base layer of liquid-impervious polymer film and a top layer of porous, hydrophylic, woven or non-woven polymer fibers, to form an animal incontinence device assembly. This may be accomplished by continuously conveying a web of the absorbent layer between continuously paid out webs of the base layer of liquid-impervious polymer film and the top layer of porous, hydrophylic, woven or non-woven polymer fibers.

The base layer of liquid-impervious polymer film, according to the present invention, may comprise any liquid-impervious polymer film. Polymers from which the base layer may be prepared include, but are not necessarily limited to, polyethylene, polypropylene, polystyrene, polyacrylate, polymethacrylate, polyvinyl chloride, polyacrylonitrile, polyvinyl acetate, polyvinyl alcohol, polyolefin, polyester, polycarbonate, polyether, polyamide, and the like, as well as derivatives, blends, and copolymers thereof. Preferred base layers of liquid-impervious polymer film comprise a polyethylene or a polypropylene. A particularly preferred polyethylene or polypropylene layer has a thickness ranging from about 0.6 to about 1.0 mil. Such polymer films are well known and commercially available.

The top layer of porous, hydrophylic, woven or non-woven polymer fibers, according to the present invention, may comprise any monolithic, flexible, porous material including, but not necessarily limited to, a non-woven or woven textile cloth or mat, a sponge material, or the like. A preferred non-woven substrate generally comprises an adhesively bonded fibrous or filamentous material having a web or carded fiber structure, or a mat in which the fibers are distributed either in a random fashion or in a substantially aligned manner. The fibers or filaments generally comprise natural materials, e.g., fibers or filaments of synthetic materials, e.g., polyolefins, polyesters, rayon, cellulose esters, polyvinyl derivatives, polyamides, and the like, as well as combinations thereof. The thickness of the top layer may vary over wide limits. A particularly preferred top layer comprises a porous, hydrophylic, spun bonded polypropylene, having a weight from about 12 to about 13.5 grams per square meter. Such top layer materials are well known in the industry, and are commercially available.

At least a portion of the animal incontinence device assembly is laminated together, by conventional laminating techniques. Preferably, at least the base layer of liquid-impervious polymer film and a top layer of porous, hydrophylic, woven or non-woven polymer fibers are sealed together at their peripheral edges, to encapsulate the intermediate absorbent layer. The base layer of liquid-impervious polymer film and a top layer of porous, hydrophylic, woven or non-woven polymer fibers may be heat sealed together by, for example, the application of heated nip rolls to the edges of the animal incontinence device assembly. Alternatively, the base layer of liquid-impervious polymer film and a top layer of porous, hydrophylic, woven or non-woven polymer fibers may be adhered at their edges by the application of a hot melt or other appropriate adhesive intermediate the perimeters of the layers.

In an alternative embodiment, the base layer of liquid-impervious polymer film may be larger in area than the top layer of porous, hydrophylic, woven or non-woven polymer fibers, so that the base layer of liquid-impervious polymer film may be folded up and over the distal edges of the top layer of porous, hydrophylic, woven or non-woven polymer fibers before sealing the animal incontinence device assembly. This may improve the fluid retention of the inventive device.

It is observed that the animal incontinence device according to the present invention has a thickness equal to about one-third of the prior art products. This is an important feature when contemplating shipping, storage, and use of the device.

The animal incontinence device according to the present invention may additionally comprise adjuvants for enhanced performance; such as, for example, fragrances or neutralizers like sodium bicarbonate. These materials may be applied to any of the layers of the device, or may be added neat to the animal incontinence device assembly before the base layer of liquid-impervious polymer film and a top layer of porous, hydrophylic, woven or non-woven polymer fibers are sealed.

The invention is more easily comprehended by reference to specific embodiments recited hereinabove, which are representative of the invention. It must be understood, however, that the specific embodiments are provided only for the purpose of illustration and that the invention may be practiced otherwise than as specifically illustrated without departing from its spirit and scope.

What is claimed is:

1. A process for preparing an animal incontinence device, comprising the steps of:
    providing a base layer of tissue;
    applying a uniform layer of superabsorbent polymer particles to a major surface of the base layer of tissue;
    applying water to the base layer of tissue having the uniform layer of superabsorbent polymer particles thereon;
    applying a cover layer of tissue over the base layer of tissue having the uniform layer of superabsorbent polymer particles thereon, to form an absorbent layer assembly;
    passing the absorbent layer assembly between a heated nip roll and a laminating roll covered with a material softer than a material of the heated nip roll after applying the water to the base layer of tissue, wherein the material covering the laminating roll is paper, the heated nip roll and the laminating roll applying a pressure to the absorbent layer assembly without crushing the superabsorbent polymer particles, to at least partially adhere together the cover layer of tissue, the uniform layer of superabsorbent polymer particles, and the base layer of tissue, to form an absorbent layer;

inserting the absorbent layer intermediate a base layer of liquid-impervious polymer film and a top layer of porous, hydrophilic, woven or non-woven polymer fibers, to form an animal incontinence device assembly; and laminating together at least a portion of the animal incontinence device assembly to form the animal incontinence device.

2. The process for preparing the animal incontinence device according to claim 1, wherein the base layer of tissue comprises multiple plies.

3. The process for preparing the animal incontinence device according to claim 1, wherein the cover layer of tissue comprises multiple plies.

4. The process for preparing the animal incontinence device according to claim 1, wherein the base layer of tissue and the cover layer of tissue are different.

5. The process for preparing the animal incontinence device according to claim 1, wherein the superabsorbent polymer particles are applied at a concentration from about 16 to about 20 grams per square meter.

6. The process for preparing the animal incontinence device according to claim 1, wherein the heated nip roll embosses a pattern onto the absorbent layer.

7. The process for preparing the animal incontinence device according to claim 1, wherein the heated nip roll has a temperature from about 130 to about 190 degrees F.

8. The process for preparing the animal incontinence device according to claim 7, wherein the temperature ranges from about 160 to about 170 degrees F.

9. The process for preparing the animal incontinence device according to claim 1, wherein the pressure used to adhere the absorbent layer together between the heated nip roll and the laminating roll is from about 35 to about 75 psi.

10. The process for preparing the animal incontinence device according to claim 9, wherein the pressure ranges from about 50 to about 60 psi.

11. The process for preparing the animal incontinence device according to claim 1, where the steps of providing the base layer of tissue and applying the uniform layer of superabsorbent polymer particles to the major surface of the base layer of tissue are repeated at least one time, and a second base layer of tissue is applied to the initial uniform layer of superabsorbent polymer particles.

12. The process for preparing the animal incontinence device according to claim 1, further comprising the step of applying adjuvant including one of a fragrance and a neutralizer to the major surface of the base layer of tissue.

13. The process for preparing the animal incontinence device according to claim 12, wherein the base layer is larger in area than the top layer, the method further comprising the steps of:

disposing an adhesive intermediate a perimeter of the top layer and a perimeter of the base layer;

folding the peripheral edge of the base layer up and over the peripheral edges of the top layer; and sealing together the base and top layers with the adhesive to encapsulate the intermediate layer with the superabsorbent polymer particles.

14. The process for preparing the animal incontinence device according to claim 13, wherein the animal incontinence device includes the base layer of liquid-impervious polymer film, the intermediate absorbent layer consisting of superabsorbent polymer particles and at least one adjuvant disposed intermediate the base layer of tissue and the cover layer of tissue, the particles bonded and secured between the base layer of tissue and the cover layer of tissue by the application of at least one of heat and pressure, and the top layer of porous, hydrophilic, woven or non-woven polymer fiber mat, wherein the base layer and the top layer are sealed together with the adhesive and encapsulate the intermediate absorbent layer with the superabsorbent polymer particles, the base layer larger in area than the top layer so that at least one of the peripheral edges of the base layer is folded up and over the peripheral edges of the top layer, the adhesive disposed intermediate the perimeters of the top and base layers to seal the base and top layers together at their peripheral edges.

15. The process for preparing the animal incontinence device according to claim 1, wherein the heated nip roll imparts an embossed pattern to the exposed major surface of the base layer of tissue, thereby causing the absorbent layer to be more pliable.

16. The process for preparing the animal incontinence device according to claim 1, wherein the step of inserting the absorbent layer intermediate the base layer and the top layer includes continuously conveying a web of the absorbent layer between continuously payed out webs of the base layer and the top layer.

17. The process for preparing the animal incontinence device according to claim 1, wherein the water is applied by spraying a mist of the water in an amount sufficient to at least partially wet an inner surface of the base layer of tissue and the superabsorbent polymer particles, and an inner surface of the cover layer of tissue is at least partially wetted by a residual amount of the water having been applied to the base layer of tissue having the uniform layer of superabsorbent polymer particles thereon.

18. The process for preparing the animal incontinence device according to claim 1, wherein a second layer of superabsorbent polymer particles followed by a second cover layer of tissue are applied over the initial cover layer of tissue.

19. The process for preparing the animal incontinence device according to claim 18, wherein the applied water is sufficient to at least partially wet all of the layers of superabsorbent polymer particles and tissue.

20. A process for preparing an animal incontinence device, comprising the steps of:

providing a base layer of tissue;

applying a uniform layer of superabsorbent polymer particles to a major surface of the base layer of tissue;

applying water to the base layer of tissue having the uniform layer of superabsorbent polymer particles thereon, the water applied by spraying a mist of the water in an amount sufficient to at least partially wet an inner surface of the base layer of tissue and the superabsorbent polymer particles;

applying a cover layer of tissue over the base layer of tissue having the uniform layer of superabsorbent polymer particles thereon, to form an absorbent layer assembly, an inner surface of the cover layer of tissue being at least partially wetted by a residual amount of the water having been applied to the base layer of tissue having the uniform layer of superabsorbent polymer particles thereon;

passing the absorbent layer assembly between a heated nip roll and a laminating roll covered with a material softer than a material of the heated nip roll after applying the water to the base layer of tissue, the heated nip roll and the laminating roll applying a pressure to the absorbent layer assembly without crushing the superabsorbent polymer particles, to at least partially adhere together the cover layer of tissue, the uniform layer of superabsorbent polymer particles, and the base layer of tissue, to form an absorbent layer, wherein the material covering the laminating roll is paper;

inserting the absorbent layer intermediate a base layer of liquid-impervious polymer film and a top layer of porous, hydrophilic, woven or non-woven polymer fibers, to form an animal incontinence device assembly; and laminating together at least a portion of the animal incontinence device assembly to form the animal incontinence device.

21. A process for preparing an animal incontinence device, comprising the steps of:

providing a base layer of tissue;

applying a uniform layer of superabsorbent polymer particles to a major surface of the base layer of tissue;

applying adjuvant including one of a fragrance and a neutralizer to the major surface of the base layer of tissue;

applying water to the base layer of tissue having the uniform layer of superabsorbent polymer particles thereon, the water applied by spraying a mist of the water in an amount sufficient to at least partially wet an inner surface of the base layer of tissue and the superabsorbent polymer particles;

applying a cover layer of tissue over the base layer of tissue having the uniform layer of superabsorbent polymer particles thereon, to form an absorbent layer assembly, an inner surface of the cover layer of tissue being at least partially wetted by a residual amount of the water having been applied to the base layer of tissue having the uniform layer of superabsorbent polymer particles thereon;

passing the absorbent layer assembly between a heated nip roll and a laminating roll covered with a material softer than a material of the heated nip roll after applying the water to the base layer of tissue, wherein the material covering the laminating roll is paper, the heated nip roll and the laminating roll applying a pressure from about 35 psi to about 75 psi to the absorbent layer assembly without crushing the superabsorbent polymer particles, to at least partially adhere together the cover layer of tissue, the uniform layer of superabsorbent polymer particles, and the base layer of tissue, to form an absorbent layer, wherein the heated nip roll imparts an embossed pattern to the exposure major surface of the base layer of tissue, thereby causing the absorbent layer to be more pliable;

inserting the absorbent layer intermediate a base layer of liquid-impervious polymer film and a top layer of porous, hydrophilic, woven or non-woven polymer fibers by continuously conveying a web of the absorbent layer between continuously payed out webs of the base layer and the top layer, to form an animal incontinence device assembly, wherein the base layer is larger in area than the top layer;

laminating together at least a portion of the animal incontinence device assembly;

disposing an adhesive intermediate a perimeter of the top layer and a perimeter of the base layer of the animal incontinence device assembly;

folding the peripheral edge of the base layer up and over the peripheral edges of the top layer; and sealing together the base and top layers with the adhesive to encapsulate the intermediate layer with the superabsorbent polymer particles to form the animal incontinence device, wherein the animal incontinence device includes the base layer of liquid-impervious polymer film, the intermediate absorbent layer consisting of superabsorbent polymer particles and at least one adjuvant disposed intermediate the base layer of tissue and the cover layer of tissue, the particles bonded and secured between the base layer of tissue and the cover layer of tissue by the application of at least one of heat and pressure, and the top layer of porous, hydrophilic, woven or non-woven polymer fiber mat, wherein the base layer and the top layer are sealed together with the adhesive and encapsulate the intermediate absorbent layer with the superabsorbent polymer particles, the base layer larger in area than the top layer so that at least one of the peripheral edges of the base layer is folded up and over the peripheral edges of the top layer, the adhesive disposed intermediate the perimeters of the top and base layers to seal the base and top layers together at their peripheral edges.

* * * * *